(12) United States Patent
Cai et al.

(10) Patent No.: US 11,147,522 B2
(45) Date of Patent: Oct. 19, 2021

(54) PHOTON COUNTING DETECTOR AND X-RAY COMPUTED TOMOGRAPHY APPARATUS

(71) Applicant: Canon Medical Systems Corporation, Otawara (JP)

(72) Inventors: Liang Cai, Vernon, IL (US); Xiaohui Zhan, Vernon Hills, IL (US); Kevin Christopher Zimmerman, Sturtevant, WI (US); Richard Thompson, Hawthorn Woods, IL (US)

(73) Assignee: Canon Medical Systems Corporation, Otawara (JP)

( * ) Notice: Subject to any disclaimer, the term of this patent is extended or adjusted under 35 U.S.C. 154(b) by 71 days.

(21) Appl. No.: 16/424,389

(22) Filed: May 28, 2019

(65) Prior Publication Data
US 2020/0069266 A1 Mar. 5, 2020

Related U.S. Application Data

(63) Continuation-in-part of application No. 16/119,854, filed on Aug. 31, 2018, now abandoned.

(30) Foreign Application Priority Data

Mar. 6, 2019 (JP) .............................. JP2019-040707

(51) Int. Cl.
*A61B 6/00* (2006.01)
*G01T 1/20* (2006.01)
(Continued)

(52) U.S. Cl.
CPC ............ *A61B 6/4241* (2013.01); *A61B 6/032* (2013.01); *A61B 6/482* (2013.01); *A61B 6/585* (2013.01); *G01T 1/2018* (2013.01); *G01T 1/247* (2013.01)

(58) Field of Classification Search
CPC ....... A61B 6/4241; A61B 6/032; A61B 6/482; A61B 6/585; A61B 6/4291; A61B 6/5205; A61B 6/4035; G01T 1/247; G01T 1/2018
See application file for complete search history.

(56) References Cited

U.S. PATENT DOCUMENTS 4,891,844 A * 1/1990 Kiri ........................ H04N 5/33
382/132
8,437,526 B2 * 5/2013 Spahn .................. A61B 6/4233
382/132

(Continued)

FOREIGN PATENT DOCUMENTS

JP 6355747 B2 6/2018

*Primary Examiner* — Christine S. Kim
(74) *Attorney, Agent, or Firm* — Oblon, McClelland, Maier & Neustadt, L.L.P.

(57) ABSTRACT

According to one embodiment, a photon-counting detector (PCD) includes a plurality of macro-pixels. The plurality of macro-pixels arranged on a semiconductor crystal has a first face and a second face. The first face and the second face are parallel. Each macro-pixel from the plurality of macro-pixels is configured to acquire projection data for generating a reconstructed image. The plurality of macro-pixels each includes at least one large micro-pixel is disposed within the each macro-pixel and at least two small micro-pixels is disposed within the each macro-pixel. Each of the at least two small micro-pixels has a surface area that is less than a surface area of the at least one large micro-pixel.

19 Claims, 10 Drawing Sheets

(51) Int. Cl.
*G01T 1/24* (2006.01)
*H01L 27/146* (2006.01)
*A61B 6/03* (2006.01)

(56) References Cited

U.S. PATENT DOCUMENTS

| | | | |
|---|---|---|---|
| 10,393,891 B2 * | 8/2019 | Iniewski | G01T 1/171 |
| 2007/0133068 A1 * | 6/2007 | Yu | H04N 5/379 |
| | | | 358/482 |
| 2009/0290680 A1 * | 11/2009 | Tumer | G01T 1/247 |
| | | | 378/62 |
| 2011/0036988 A1 * | 2/2011 | Campbell | H01L 27/14676 |
| | | | 250/370.07 |
| 2015/0185333 A1 | 7/2015 | Cho | |
| 2015/0323685 A1 | 11/2015 | Nelson et al. | |
| 2015/0348290 A1 * | 12/2015 | Yl | A61B 6/5205 |
| | | | 378/98 |
| 2017/0090047 A1 | 3/2017 | Shahar et al. | |
| 2018/0180748 A1 | 6/2018 | Shahar et al. | |
| 2019/0029628 A1 * | 1/2019 | Konno | A61B 6/5258 |
| 2019/0076101 A1 * | 3/2019 | Pan | A61B 6/032 |

* cited by examiner

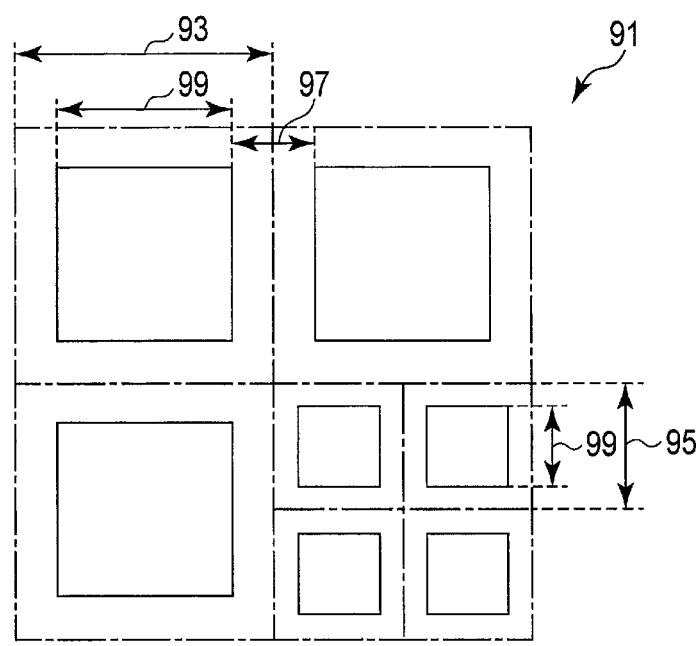
F I G. 6

PHOTON COUNTING DETECTOR AND X-RAY COMPUTED TOMOGRAPHY APPARATUS

CROSS-REFERENCE TO RELATED APPLICATIONS

This application is a Continuation-in-Part Application of U.S. patent application Ser. No. 16/119,854, filed Aug. 31, 2018, and based upon and claiming the benefit of priority from the prior Japanese Patent Application No. 2019-040707, filed Mar. 6, 2019, the entire contents all of which are incorporated herein by reference.

FIELD

Embodiments described herein relate generally to a photon counting detector and an X-ray computed tomography apparatus.

BACKGROUND

Photon-counting computed tomography (CT) is a computed tomography technique with the potential to significantly improve existing CT imaging techniques. A photon-counting CT system includes a photon-counting detector which registers the interactions of individual photons. By keeping track of the deposited energy in each interaction, the detector pixels of a photon-counting CT detector each record an approximate energy spectrum or counts in energy bins. In contrast, typical CT scanners use energy-integrating detectors, where the total energy deposited in a pixel during a fixed period of time is registered.

There are several challenges to incorporating photon-counting detectors in CT systems. The challenges are related to demands on detector material and electronics resulting from large data volumes and count rates. As an example, each $mm^2$ of a CT detector may receive several hundred million photon interactions per second during a scan. To avoid saturation in areas where little material is present between the X-ray source and the detector, the pulse resolving time must be small compared to the average time between photon interactions in a pixel. Even before saturation, the detector functionality starts to deteriorate because of pulse pileup, where two (or more) photon interactions take place in the same pixel too close in time to be resolved as discrete events. Such quasi-coincident interactions lead to a loss of photon counts and distort the pulse shape. Due to these effects, the demands on the physical response time of the detector material as well as on the electronics responsible for pulse-shaping, binning and recording pixel data become very high.

Photon-counting detectors may be manufactured with smaller pixel size than approximately $1\times1$ $mm^2$ without compromising dose efficiency. Using smaller image pixels decreases the per-pixel count rate and thus alleviates the demands on pulse resolving time at the expense of requiring more electronics. Pixel size and the corresponding readout electronics design are key parts in a photon-counting detector design. For high-flux scanning environment including several hundred million photon interactions per second during a CT scan, a smaller pixel size for a photon counting detector (PCD) is preferred. In general, pixel size for photon counting CT applications may range from 150 μm pitch to 500 μm pitch. The pixel pitch is the distance from the center of one pixel to the center of the next pixel. The lower the pixel pitch distance, the closer the pixels. A smaller pixel design may consist of pixels having less than 500 μm pitch for photon counting CT applications. The smaller pixel design for the PCD is desirable in high-flux cases because it is relatively immune to the pulse pileup. However, one issue associated with the use of smaller pixels is the degradation of the detector response due to severe charge sharing and signal cross talk.

Partial energy deposition and single photons causing signals in multiple pixels poses a challenge in photon-counting CT. Charge sharing, where an interaction takes place close to a pixel boundary, causing the released energy to be shared between neighboring pixels and thus be interpreted as several lower-energy photons, is one cause of such events. Charge sharing results in a distorted energy spectrum. In contrast to saturation and pileup effects, issues caused by partial energy deposition and multiple interacting photons are aggravated by smaller pixel size.

Using larger pixel size for the PCD is one solution that provides less charge sharing and cross talk effect, based on which the detector response is typically better. The portion of peak energy leaking to lower energy part is smaller, and this may result in an improvement to material decomposition. Thus, using a larger pixel size such as a pixel with a 500 μm pitch may be preferable in a low-flux scanning environment. One possible disadvantage of using a large pixel design for the PCD is that it puts a significant burden on electronics or other post-processing aspects to deal with severe pulse pileup. Therefore, from a material decomposition noise point of view, small pixel size may be preferable in high-flux scanning environments and large pixel size may be preferable in low-flux scanning environments. In a photon-counting CT scanning environment, the PCD is typically exposed to both high-flux and low-flux during a scan of a patient. The PCD in a photon-counting CT scanner using a small pixel design may perform well for high-flux, but may perform inadequately in a low-flux scenario. The PCD in a photon-counting CT scanner using a large pixel design may perform well for the low-flux scenario, but may perform inadequately in a high-flux scenario.

Thus, there is a need in the art for photon-counting CT detectors that perform well in both high-flux and low-flux CT scanning environments by minimizing pulse pileup issues associated with the use of larger pixels in the PCD as well as minimizing charge sharing issues associated with the use of smaller pixels in the PCD.

BRIEF DESCRIPTION OF THE DRAWINGS

FIG. 6 illustrates a configuration example of an X-ray detector in accordance with the present disclosure;

DETAILED DESCRIPTION

The present disclosure is directed to a CT detector apparatus for use in a scan environment that may include both high flux and low flux that is relatively immune to pulse pile up while maintaining an adequate detector response by reducing charge sharing. The CT detector apparatus is able to perform well in both high flux and low flux scenarios by using a photon counting detector (PCD) that implements a hybrid pixel pattern design.

In general, according to one embodiment, a photon-counting detector (PCD) includes a plurality of macro-pixels. The plurality of macro-pixels arranged on a semiconductor crystal has a first face and a second face. The first face and the second face are parallel. Each macro-pixel from the plurality of macro-pixels is configured to acquire projection data for generating a reconstructed image. The plurality of macro-pixels each includes at least one large micro-pixel is disposed within the each macro-pixel and at least two small micro-pixels is disposed within the each macro-pixel. Each of the at least two small micro-pixels has a surface area that is less than a surface area of the at least one large micro-pixel.

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

The present disclosure is directed to a photon-counting detector (PCD) employed in a photon-counting CT system. The term PCD is used interchangeably throughout the present disclosure with the term detector. When a photon-counting CT system scans a patient or object, the scanning environment may continuously change from a high flux to a low flux scanning environment or vice versa. The PCD with a hybrid pixel pattern design discussed throughout the present disclosure is relatively immune to pulse pileup while maintaining an adequate detector response by reducing charge sharing even during dynamic changing of the scanning environment where the PCD is exposed to both high flux and low flux scanning environments.

Figure 2A:
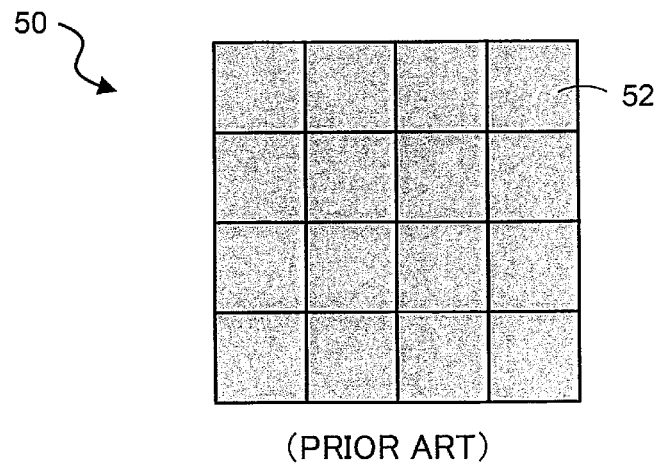
FIG. 2A illustrates a schematic diagram of a uniform pixel pattern design used in a photon-counting detector.
Figure 2B:
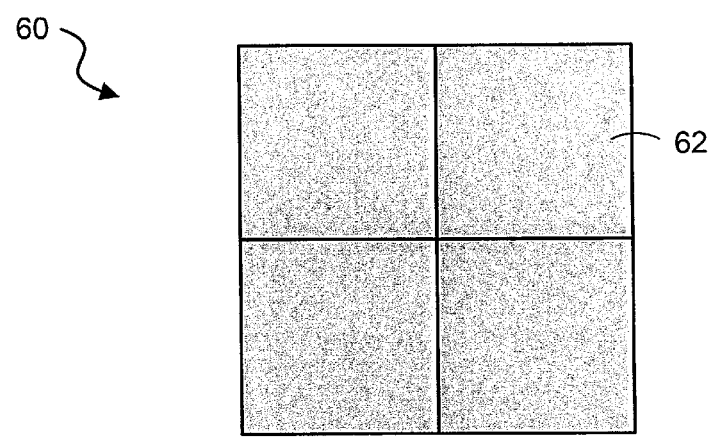
FIG. 2B illustrates a schematic diagram of another uniform pixel pattern design used in a photon-counting detector.

The uniform pixel pattern design shown in FIG. 2A shows one macro-pixel 50 with sixteen equally sized micro-pixels 52. If the surface area of the macro-pixel 50 is 1 mm², then the pixel size of the sixteen equally sized micro-pixels are 250 μm. The detector response in this example may take on the characteristics associated with a pixel size of 250 μm such as the benefit of relative immunity to pulse pileup in a high flux scanning environment and the disadvantage of severe charge sharing in a low flux scanning environment. In FIG. 2B the one macro-pixel 60 also includes a uniform pixel pattern design with four equally sized micro-pixels 62. If the surface area of the macro-pixel 60 is the same as the macro-pixel 50 in FIG. 2A, then the pixel size of the four equally sized micro-pixels are 500 μm. The detector response in this example may take on the characteristics associated with a pixel size of 500 μm such as the benefit of minimal charge sharing in a low flux scanning environment and the disadvantage of increased pulse pileup in a high flux scanning environment. Thus, using a uniform pixel pattern design for a plurality of macro-pixels on a PCD may not be well suited for a scanning environment that includes both high flux and low flux.

The hybrid pixel pattern design for each macro-pixel within a PCD described throughout the present disclosure is designed for both high flux and low flux scanning environments by implementing a non-uniform pixel pattern design consisting of at least two different sized micro-pixels. The hybrid pixel pattern design of the macro-pixels may be implemented on a PCD which is included in a photon-counting CT scanning system as described below with reference to FIG. 1.

Figure 1:
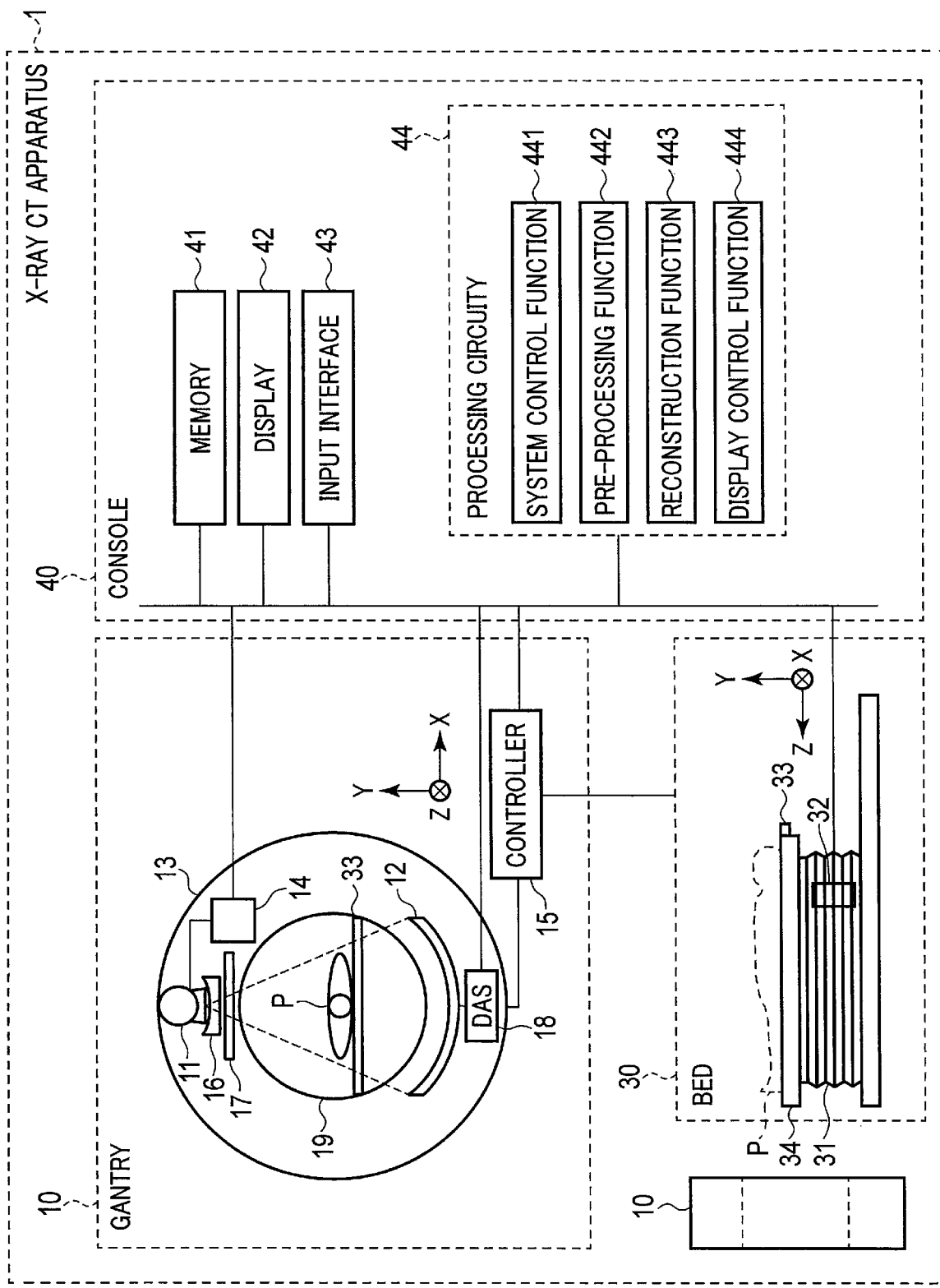
FIG. 1 illustrates a schematic diagram of an implementation of a computed tomography (CT) scanner.

An X-ray computed tomography (CT) that includes a medical imaging processing apparatus according to this embodiment will be described with reference to the block diagram of FIG. 1. The X-ray CT apparatus 1, shown in FIG. 1, includes a gantry 10, a bed 30, and a console 40 that implements the processing of the medical imaging processing apparatus. For the sake of explanation, FIG. 1 shows multiple gantries 10.

In the present embodiment, the rotation axis of a rotation frame 13 in the non-tilted state, or the longitudinal direction of a table top 33 of the bed 30, is defined as a "Z-axis direction"; the axial direction orthogonal to the Z-axis direction and horizontal to the floor is defined as an "X-axis direction"; and the axial direction orthogonal to the Z-axis direction and vertical to the floor is defined as a "Y-axis direction".

For example, the gantry 10 and the bed 30 are installed in a CT examination room, and the console 40 is installed in a control room adjacent to the CT examination room. The console 40 is not necessarily installed in the control room. For example, the console 40 may be installed together with the gantry 10 and the bed 30 in the same room. In any case, the gantry 10, the bed 30, and the console 40 are communicably connected to one another by wire or radio.

The gantry 10 is a scanner with a configuration for performing X-ray CT imaging on a subject P. The gantry 10 includes an X-ray tube 11, an X-ray detector 12, a rotation frame 13, an X-ray high voltage device 14, a controller 15, a wedge filter 16, a collimator 17, and a data acquisition system (DAS) 18.

The X-ray tube 11 is a vacuum tube that generates X-rays by emitting thermal electrons from the cathode (filament) to the anode (target) in response to application of a high voltage and supply of a filament current from the X-ray high voltage device 14. Specifically, X-rays are generated by the thermal electrons colliding with the target. Examples of the X-ray tube 11 include a rotating anode type X-ray tube that generates X-rays by emitting thermal electrons to the rotating anode. The X-rays generated in the X-ray tube 11 are, for example, formed into a cone-beam shape by the collimator 17, and applied to the subject P.

The X-ray detector 12 detects X-rays that have been emitted by the X-ray tube 11 and have passed through the subject P, and outputs an electrical signal corresponding to the X-ray dose to the DAS 18. The X-ray detector 12 includes a plurality of X-ray detection element lines, each including a plurality of X-ray detection elements aligned in a channel direction along an arc having a center at the focus of the X-ray tube 11, for example. The X-ray detector 12 has an array structure in which a plurality of X-ray detection element lines, each including a plurality of X-ray detection elements aligned in the channel direction, are aligned in a slice direction (row direction).

Specifically, the X-ray detector 12 may be, for example, an indirect conversion type detector including a grid, a scintillator array, and an optical sensor array, or may be a direct conversion type detector including a semiconductor element that converts incident X-rays into an electrical signal as will be described with reference to FIG. 4A onward. The X-ray detector 12 is an example of the PCD according to the present embodiment, and will also be referred to as a "PCD 12".

The scintillator array includes a plurality of scintillators. The scintillator converts the applied X-rays into photons of a number corresponding to the intensity of the applied X-rays.

The grid is arranged on the surface of the scintillator array on the X-ray incident side, and includes an X-ray shielding plate having the function of absorbing scattered X-rays. The grid may be referred to as a "collimator".

The optical sensor array has the function of amplifying and converting light received from the scintillator into an electrical signal to generate an output signal (energy signal) having a peak value corresponding to the energy of the applied X-rays, and includes an optical sensor, such as a photomultiplier (PMT).

The rotation frame 13 supports an X-ray generator and the X-ray detector 12 rotatably around a rotation axis. Specifically, the rotation frame 13 is an annular frame that supports the X-ray tube 11 and the X-ray detector 12 in such a manner that the X-ray tube 11 faces the X-ray detector 12, and rotates the X-ray tube 11 and the X-ray detector 12 under the control of a controller 15 to be described later. The rotation frame 13 is rotatably supported by a stationary frame (not shown) made of a metal such as aluminum. Specifically, the rotation frame 13 is connected to an edge portion of the stationary frame via a bearing. The rotation frame 13 rotates around the rotation axis Z at a predetermined angular velocity while receiving power from a driver of the controller 15.

In addition to the X-ray tube 11 and the X-ray detector 12, the rotation frame 13 includes and supports the X-ray high voltage device 14 and the DAS 18. Such a rotation frame 13 is housed in an approximately-cylindrical case with a bore 19 constituting an imaging space. The bore approximately corresponds to the FOV. The central axis of the bore corresponds to the rotation axis Z of the rotation frame 13. Detection data generated by the DAS 18 is transmitted, for example, from a transmitter including a light-emitting diode (LED) to a receiver (not shown) including a photodiode, and arranged on a non-rotating portion (such as the stationary frame, illustration omitted in FIG. 1) of the gantry by optical communication, and then transferred to the console 40. The method of transmitting detection data from the rotation frame to the non-rotating portion of the gantry is not limited to the above-described optical communication, and may be any scheme as long as the transmission is non-contact type data transmission.

The X-ray high voltage device 14 includes: a high voltage generator including electrical circuitry such as a transformer, a rectifier, etc. and having the function of generating a high voltage to be applied to the X-ray tube 11 and a filament current to be supplied to the X-ray tube 11; and an X-ray controller configured to control an output voltage in accordance with the X-rays emitted by the X-ray tube 11. The high voltage generator may be of a transformer type, or an inverter type. The X-ray high voltage device 14 may be provided in the rotation frame 13 to be described later, or in the stationary frame (not shown) of the gantry 10.

The controller 15 includes processing circuitry including a central processing unit (CPU), etc., and a driver such as a motor or an actuator, etc. The processing circuitry includes, as hardware resources, a processor, such as a CPU or a micro processing unit (MPU), and a memory, such as a read only memory (ROM) or a random access memory (RAM). The controller 15 may be realized by an application specific integrated circuit (ASIC), a field programmable gate array (FPGA), or another complex programmable logic device (CPLD) or simple programmable logic device (SPLD). The controller 15 controls the X-ray high voltage device 14 and the DAS 18, etc. in accordance with instructions from the console 40. The processor implements the above control by reading and executing a program stored in the memory.

The CPU may execute a computer program including a set of computer-readable instructions that perform the functions described herein, and the program is stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor and an operating system known to those skilled in the art. Further, the CPU can be implemented as multiple processors cooperatively working in parallel to perform the instructions.

The controller 15 also has the function of performing operation control of the gantry 10 and the bed 30 in response to an input signal from an input interface 43 to be described later attached to the console 40 or the gantry 10. For example, the controller 15 performs control to rotate the rotation frame 13, control to tilt the gantry 10, or control to operate the bed 30 and the table top 33 in response to an input signal. The control to tilt the gantry 10 is implemented by the controller 15 rotating the rotation frame 13 around an axis parallel to the X-axis direction, based on tilt angle information input through the input interface 43 attached to the gantry 10. The controller 15 may be provided either in the gantry 10 or in the console 40. The controller 15 may be configured by directly integrating a program in the circuitry of the processor, instead of storing a program in the memory. In this case, the processor implements the above-described control by reading and executing the program integrated in the circuitry.

The wedge filter 16 is a filter for adjusting the dose of X-rays emitted from the X-ray tube 11. Specifically, the wedge filter 16 is a filter that allows X-rays emitted from the X-ray tube 11 to pass therethrough, and attenuates the X-rays so that the X-rays emitted from the X-ray tube 11 to the subject P exhibit predetermined distribution. For example, the wedge filter 16 (or bow-tie filter) is a filter obtained by processing aluminum so that it has a predetermined target angle and a predetermined thickness.

The collimator 17 is lead plates or the like for narrowing the application range of X-rays that have passed through the wedge filter 16, and includes a slit formed by combining the lead plates or the like. The collimator 17 may be referred to as an "X-ray diaphragm".

The DAS 18 generates digital data indicating counts of X-rays detected by the X-ray detector 12 (also referred to as "detection data") for each of a plurality of energy bands (referred to as "energy bins" or simply as "bins"). The detection data is a set of a channel number and row number of a source X-ray detection element, a view number indicating a collected view (also referred to as a projection angle), and data of the count value identified by the energy bin number. The DAS 18 is implemented by, for example, an application specific integrated circuit (ASIC) on which a circuit element capable of generating detection data is mounted. The detection data is transferred to the console 40.

For example, the DAS 18 includes a preamplifier, a variable amplifier, integrating circuitry, and an A/D converter for each detector pixel. The preamplifier amplifies the electrical signal from the connected X-ray detection element with a predetermined gain. The variable amplifier amplifies the electrical signal from the preamplifier with a variable gain. The integrating circuitry integrates electrical signals from the preamplifier for one view period to generate an integral signal. The peak value of the integral signal corresponds to the dose value of X-rays detected by the connected X-ray detection element for one view period. The A/D converter performs A/D conversion on the integral signal from the integrating circuitry to generate detection data.

The bed 30 is a device to place thereon the subject P to be scanned and move the subject P, and includes a base 31, a bed actuator 32, a table top 33, and a support frame 34.

The base 31 is a case that supports the support frame 34 movably in the vertical direction.

The bed actuator 32 is a motor or actuator that moves the table top 33 on which the subject P is placed in the longitudinal direction of the table top 33. The bed actuator 32 moves the table top 33 in accordance with control by the console 40 or control by the controller 15. For example, the bed actuator 32 moves the table top 33 in the direction orthogonal to the subject P so that the body axis of the subject P placed on the table top 33 matches the central axis of the bore of the rotation frame 13. The bed actuator 32 may also move the table top 33 in the body axis direction of the subject P in accordance with X-ray CT imaging performed using the gantry 10. The bed actuator 32 generates power by driving at a rotation speed corresponding to the duty ratio of the drive signal from the controller 15. The bed actuator 32 is implemented by a motor, such as a direct drive motor or a servo motor.

The table top 33 provided on the top surface of the support frame 34 is a plate on which the subject P is placed. The bed actuator 32 may move not only the table top 33 but the support frame 34 in the longitudinal direction of the table top 33.

The console 40 includes a memory 41, a display 42, an input interface 43, and processing circuitry 44. Data communication between the memory 41, the display 42, the input interface 43, and the processing circuitry 44 is performed via a bus. The console 40 is described as being separate from the gantry 10, but the gantry 10 may include the console 40 or part of each constituent element of the console 40.

The memory 41 is a storage device, such as a hard disk drive (HDD), a solid state drive (SSD), or an integrated circuit storage device, etc., which stores various types of information. The memory 41 stores, for example, projection data and reconstructed image data. The memory 41 may be not only the HDD, SSD, or the like, but a driver that writes and reads various types of information in and from, for example, a portable storage medium such as CD, DVD, or a flash memory, or a semiconductor memory such as a random access memory (RAM). The storage area of the memory 41 may be in the X-ray CT apparatus 1, or in an external storage device connected via the network. For example, the memory 41 stores data of a CT image or a display image. The memory 41 also stores a control program according to the present embodiment.

The display 42 displays various types of information. For example, the display 42 outputs a graphical user interface (GUI) or the like for receiving a medical image (CT image) generated by the processing circuitry 44, and various types of operations from the operator. For the display 42, for example, a liquid crystal display (LCD), a cathode ray tube (CRT) display, an organic electro luminescence display (OELD), a plasma display, or any other display can be used as appropriate. The display 42 may be provided in the gantry 10. The display 42 may either be a desktop type or configured by a tablet device capable of wirelessly communicating with the console 40.

The input interface 43 receives various types of input operations from the operator, converts a received input operation into an electrical signal, and outputs the electrical signal to the processing circuitry 44. For example, the input interface 43 receives, from the operator, a collection condition for collecting projection data, a reconstruction condition for reconstructing a CT image, and an image-processing condition for generating a post-processing image from the CT image, etc. For the input interface 43, for example, a mouse, a keyboard, a trackball, a switch, a button, a joystick, a touch pad, or a touch panel display can be used as appropriate. In the present embodiment, the input interface 43 does not necessarily include a physical operation component such as a mouse, a keyboard, a trackball, a switch, a button, a joystick, a touch pad, or a touch panel display. For example, the input interface 43 also includes electrical signal processing circuitry that receives an electrical signal corresponding to an input operation from an external input device provided separately from the apparatus, and outputs the electrical signal to the processing circuitry 44. The input interface 43 may be provided in the gantry 10. The input interface 43 may be configured by a tablet device capable of wirelessly communicating with the console 40.

The processing circuitry 44 controls the overall operation of the X-ray CT apparatus 1 in accordance with the electrical signal of the input operation output from the input interface 43. For example, the processing circuitry 44 includes, as hardware resources, a processor such as a CPU, an MPU, or a graphics processing unit (GPU), and a memory such as a ROM or a RAM. With a processor that executes a program loaded into the memory, the processing circuitry 44 performs a system control function 441, a pre-processing function 442, a reconstruction function 443, and a display control function 444. Each of the functions (the system control function 441, the pre-processing function 442, the reconstruction function 443, and the display control function 444) is not necessarily implemented by a single processing circuit. Processing circuitry may be configured by combining a plurality of independent processors, and the processors may execute respective programs to implement the functions.

The system control function 441 controls each function of the processing circuitry 44 based on an input operation received from the operator via the input interface 43. Specifically, the system control function 441 reads a control program stored in the memory 41, loads it into a memory in the processing circuitry 44, and controls each part of the X-ray CT apparatus 1 in accordance with the loaded control program. For example, the processing circuitry 44 performs each function of the processing circuitry 44 based on an input operation received from the operator via the input interface 43. For example, the system control function 441 obtains a two-dimensional positioning image of the subject P to determine the scan range, imaging condition, etc. The positioning image may also be referred to as a "scanogram" or "scout image".

The pre-processing function 442 generates data obtained by performing pre-processing on detection data output from the DAS 18, such as logarithmic conversion processing, offset correction processing, processing for sensitivity correction between channels, beam hardening correction, and correction for detector calibrations, detector nonlinearities, polar effects, noise balancing, and material decomposition. Data (detection data) before pre-processing and data after pre-processing may be collectively referred to as "projection data". The pre-processing function 442 is an example of the pre-processor.

The reconstruction function 443 generates CT image data by performing reconstruction processing using a filtered back projection method, a successive approximation reconstruction method, a stochastic image reconstruction method, or the like, on the projection data generated by the pre-processing function 442. The reconstruction function 443 is an example of the reconstruction processor. Image filtering, smoothing, volume rendering, or image differential processing may be applied to the CT image data if required. The display control function 444 converts CT image data generated by the reconstruction function 443 into tomographic image data of a given cross section, or three-dimensional image data by a publicly-known method, based on the input operation received from the operator via the input interface 43. The generation of three-dimensional image data may be performed directly by the reconstruction function 443. The display control function 444 is an example of the display controller.

In one implementation, the X-ray tube 11 is a single source emitting a broad spectrum of X-ray energies.

The PCD 12 can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pileup of detection events may occur. The energy of a detected X-ray is proportional to the signal generated by the direct detector, and the detection events can be organized into energy bins yielding spectrally resolved X-ray data for spectral CT.

In the present disclosure, the signals from the PCD 12 are collected by a readout circuit not illustrated. The readout channel outputs an analog signal that is processed by a preamplifier and is then inputted into an analog-to-digital (A/D) converter. The A/D converter is clocked at a high frequency (typically 40 to 100 MHz) and outputs a digital signal. The digital signal is then transferred to the processor 24 for detecting the incident photons. Digital samples are processed by an algorithm implemented in a digital filter that determines the time-stamp and amplitude of the signal. The readout circuit continuously samples analog signals and produces large data sets to be further processed in an image processing chain.

The disclosed embodiments facilitate the use of thinner detectors (e.g., W<2.0 mm) with larger thickness (T~3.0 mm), which improves charge-collection efficiency, maintaining a higher operating field with no charge loss at the surface. A weighting potential describes the coupling between the moving charges and the electrode of a charge when the moving charges drift in the detector.

Figure 3A:
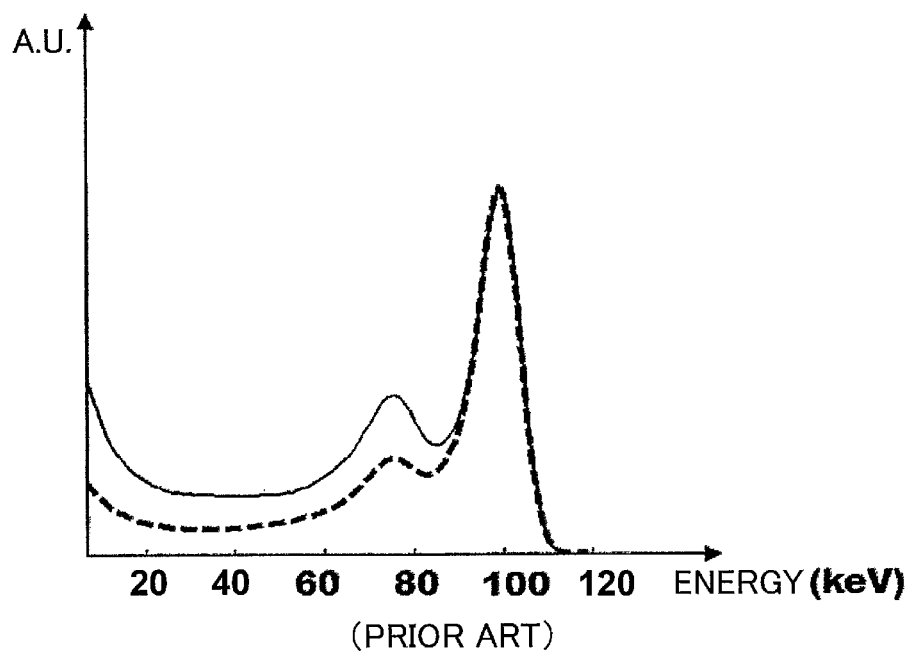
FIG. 3A is a graph showing an example of two different detector responses for two different pixel sizes.

Referring now to FIG. 3A, the graph illustrates an example of a 100 kilo electron-volts (keV) x-ray response for a PCD including a uniform pixel pattern design with a pixel size of 500 µm pixels and an x-ray response for a PCD including a uniform pixel pattern design with a pixel size of 250 µm pixels. The solid line represents the PCD having the 250 µm pixels and the dashed line represent a PCD having the 500 µm pixels. Both PCDs include a thickness of 2 mm and both PCD's include macro-pixels with a surface area of 1 $mm^2$ by way of example. A macro-pixel having a uniform pixel pattern design with a pixel size of 500 µm would include 4 micro-pixels within a macro-pixel having a surface area of 1 $mm^2$. A macro-pixel having a uniform pixel pattern design with a pixel size of 250 µm pixels would include 16 micro-pixels within a macro-pixel having an area of 1 $mm^2$. The dashed line represents a PCD with a uniform pixel size of 500 µm. The two different pixel sizes of 250 µm and 500 µm are shown to illustrate the different detector responses due to pixel size.

The vertical axis of the graph shown in FIG. 3A reflects the counts or percentage detected at specific energies for a 100 keV input. The graph shows that the 250 µm pixel has higher charge sharing events. An ideal detector would have a detector response representative of a delta function. The graph illustrates how pixel size and the corresponding readout electronics are important considerations for PCD design.

The PCD having a uniform pixel pattern design with the smaller micro-pixels in the example of FIG. 3A is desirable for a high flux scanning environment that may consist of several hundred million photo interactions per second per square millimeter. One advantage related to the smaller micro pixels is the relative immunity to pulse pileup issues. However, the smaller pixel size appears to be more susceptible to the degrading of the detector response due to severe charge sharing that may happen as illustrated in the graph of FIG. 3A. The larger pixel size such as 500 µm in the example may provide less charge sharing and cross talk effect, which may result in improved detector response. The portion of peak energy leaking to a lower energy part is smaller, which can reduce material decomposition. However, the larger micro-pixel design increases the burden on the electronics or other post processing to deal with severe pulse pileup.

Figure 3B:
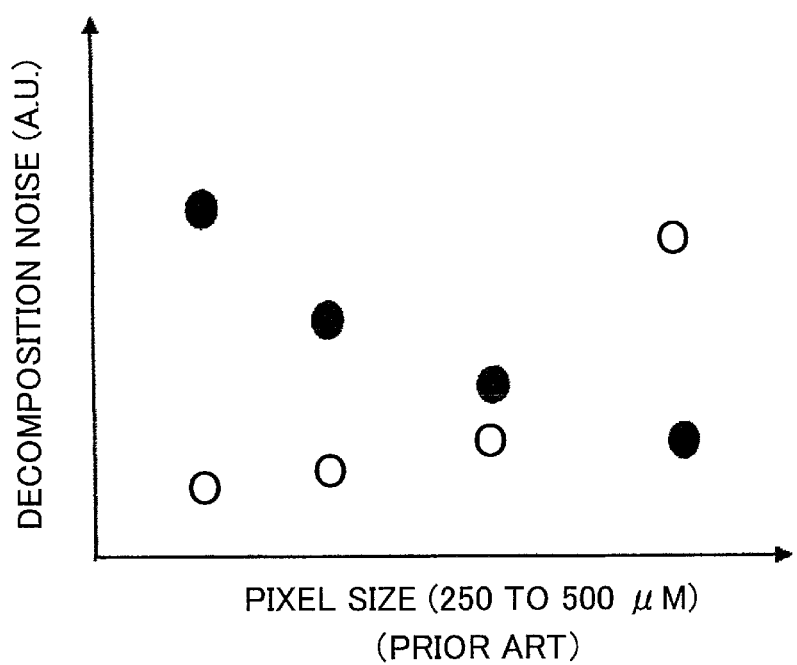
FIG. 3B is a graph showing an example of a relationship between decomposition noise and pixel size under high flux and low flux.

From a material decomposition noise view, small pixel size is preferred in high flux scanning environments and large pixel size is preferred in low flux scanning environments as illustrated in the graph shown in FIG. 3B. The graph in FIG. 3B illustrates the relationship between decomposition noise and pixel size in high flux and low flux scanning environments. The vertical axis of the graph in FIG. 3B represents decomposition noise and the horizontal axis represent a pixel size range between 250-500 µm. The solid plot points reflect the level of decomposition noise in a low flux scanning environment as pixel size increases and the hollow points reflect the level of decomposition noise in a high flux scanning environment as pixel size increases. According to the graph of FIG. 3B, the plot points reveal that in a high flux scanning environment as pixel size increases so does decomposition noise and in a low flux scanning environment the decomposition noise decreases with an increase in pixel size. Thus, using a detector with a uniform pixel size design including small pixels or large pixels may result in certain advantages and disadvantages.

Figure 4A:
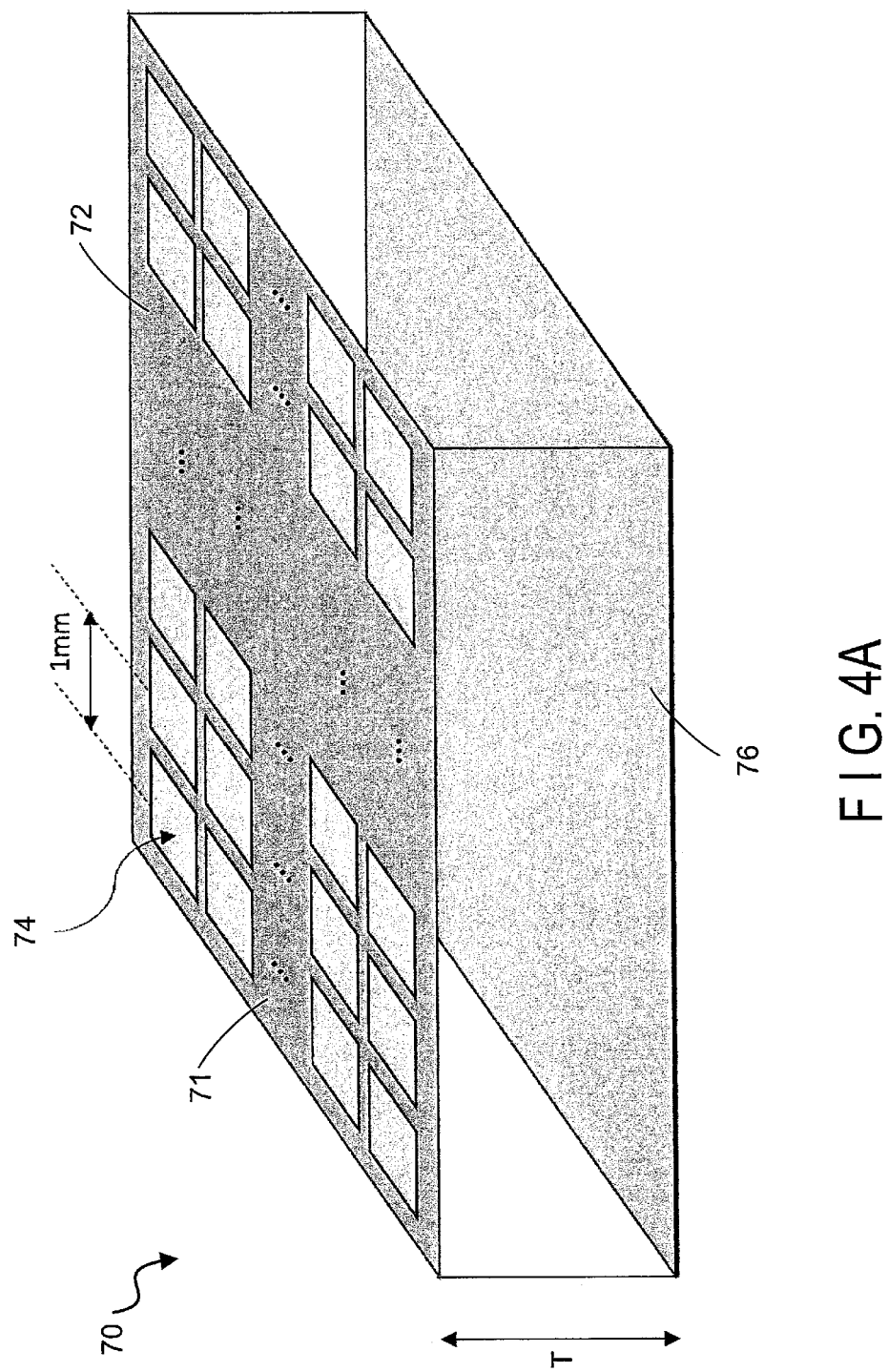
FIG. 4A is a perspective view of a photon-counting detector including a plurality of pixels in accordance with the present disclosure.

Referring now to FIG. 4A, a photon-counting detector array 70 including a plurality of macro-pixels with a hybrid pixel pattern design is shown. The photon-counting detector array 70 includes a crystal 71 formed from a semiconductor material, such as CdZnTe or CdTe. One surface of the crystal 71 has a large single-cathode electrode 76. The opposite surface of the crystal is the anode surface 72, and includes an array of rectangular or square anode pixels 74. The hybrid pixel pattern design is used to obtain the benefits of using a small pixel size design as well as a large pixel size design while minimizing any disadvantages associated with the use of either a small pixel size design or a large pixel size design. The thickness of the detector array 70 is represented by T. In one example of the present disclosure, the thickness of the detector array 70 is 3 mm for sufficient stopping power of the x-ray. However, the thickness of the detector array 70 may vary depending on the type of application, semiconductor material and other considerations associated with detector design. Each individual pixel 74 of the detector array 70 is a macro-pixel with a hybrid pixel pattern design. While each macro-pixel on the detector array 70 is of uniform size, the macro-pixels include micro-pixels of varying size. The quantity of macro-pixels on the detector array 70 may vary depending on vendor design. For example the detector may include a 12×8 array of macro-pixels (96 pixels), a 12×12 array of macro-pixels (96 pixels) or a 16×16 array of macro-pixels (256 pixels) by way of some examples and not intended to limit the array of macro-pixels associated with a particular detector.

In one example, the macro-pixels of the detector array 70 shown in FIG. 4A has an area of 1 mm×1 mm. The area of the macro-pixel can be any size and is not limited to a 1 mm×1 mm area.

Figure 4B:
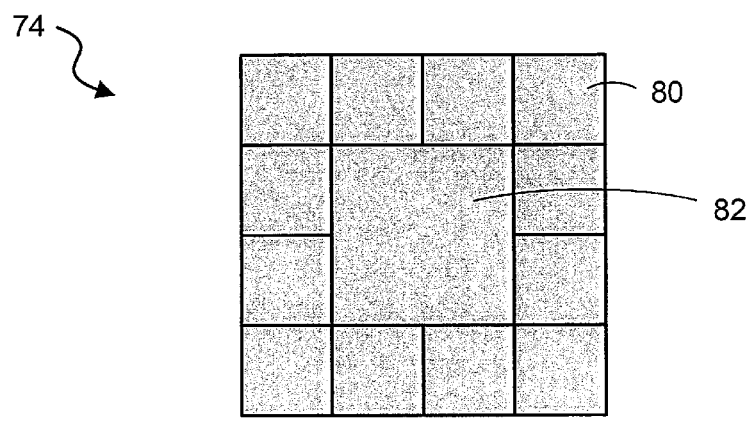
FIG. 4B is a schematic diagram of a hybrid pixel pattern design for each pixel in the photon-counting detector of FIG. 4A in accordance with the present disclosure.

The present disclosure minimizes pulse pileup and charge-sharing issues by using a hybrid pixel pattern design which consists of non-uniform micro-pixels within a macro-pixel as shown by way of example in FIG. 4B. FIG. 4B includes a macro-pixel 74 with a hybrid pixel pattern design. The macro-pixel 74 includes two different sized micro-pixels. In this example there is one large micro-pixel 82 within the macro-pixel 74 surrounded by twelve smaller micro-pixels 80. The macro-pixel 74 in this example consists of 13 total micro-pixels. If the macro-pixel 74 in this example has an area of 1 mm×1 mm, then the large micro-pixel 82 has a surface area that is four times greater than the surface area of one of the smaller micro-pixels 80. In this example the smaller micro-pixels have a 250 µm size and the large micro-pixel has a 500 µm size. The hybrid pixel pattern design for the macro-pixel 74 may rely substantially on the 250 µm micro-pixels 80 during a high flux scanning environment to avoid pulse pileup issues while relying substantially on the one larger 500 µm micro-pixel 82 in a low flux scanning environment to minimize charge sharing and cross talk between the micro-pixels of the macro-pixel 74. The larger micro-pixel 82 is expected to provide better information in low flux scanning environment and the smaller micro-pixels 80 are expected to provide better information in high flux scanning environments. In other words, information obtained from the first set of detector responses corresponding to at least one large micro-pixel 82 may be used to calibrate at least two small micro-pixels 80 in a low-flux scanning environment. In contrast, information obtained from the second set of detector responses corresponding to at least two small micro-pixels 80 may be used to calibrate at least one large micro-pixel 82 in a high-flux scanning environment. The detector response for both large and small micro-pixels within the macro-pixel is used regardless of the type of scanning environment (high flux/low flux).

Unlike a uniform pixel size design for a macro-pixel, a hybrid pixel pattern design allows for a good balance between large and small micro-pixels. From the Shockley-Ramo theorem, the weighting field and weighting potential for each macro-pixel would be determined only by the micro-pixel size itself. The hybrid pixel pattern is a detector pattern that contains pixels of more than one size for the purpose of optimizing the detector's spectral photon counting performance across a range of input flux rates. In the above example the hybrid pixel pattern design for the macro-pixel included two different sized micro-pixels. However, the macro-pixel of the hybrid pixel pattern design may include three different sized micro-pixels or four different sized micro-pixels. The detector response increases in complexity with three or four different sized micro-pixels within a macro-pixel.

Although the example described a smaller micro-pixel having a 250 µm size, various sizes may be used for the smaller micro-pixels such 225 µm size, 200 µm size, 175 µm size, 150 µm size, etc. The size of a smaller micro-pixel may range from approximately 150 µm to approximately 300 µm. Typically, a size of 250 µm or less may be used for a smaller micro-pixel size design associated with desirable results in high flux scanning environments. Although the example described a larger micro-pixel having a 500 µm size, various sizes may be used for the larger micro-pixels such as 450 µm size, 400 µm size, 350 µm size, 300 µm size, etc., and a size may range from approximately 300 µm to approximately 600 µm.

A size is determined so that the large micro-pixel and the small micro-pixel have a relationship of similarity. For example, the large micro-pixel and the small micro-pixel may have a relationship in which a half-length of one side of the macro-pixel corresponds to the length of at least one side of the large micro-pixel, while a half-length of one side of the large micro-pixel corresponds to the length of at least one side of the small micro-pixel. Thus, the small micro-pixels and the large micro-pixels may have a self-similarity relationship. The large micro-pixels and the small micro-pixels having the self-similarity relationship are filled on the detection surface of the X-ray detector 12.

There are various combinations of two different sized micro-pixels that may be used within a macro-pixel.

In general there is no definitive rule to the smallest pixel size for the smaller micro-pixels. However, charge sharing effect increases as the pixel size gets smaller. Pixel size smaller than 150 µm size may not be of interest for CT applications. Each micro-pixel has an electronics readout channel to handle the signal from specific micro-pixel. Application Specific Integrated Circuit (ASIC) is often used for such applications. Each electronics channel typically includes a pre-amplifier, shaper (such as a CR-RC shaper) or high/low pass filter and digitizer to record event amplitude (implemented by analog to digital converted or comparator). For most readout electronics, for example ASIC, typically all readout channels are of the same physical size. The readout channels of different physical size to match the hybrid pixel pattern design of the detector may be used or readout channels with the same physical size may be used with the help of an interposer.

Figure 5A:
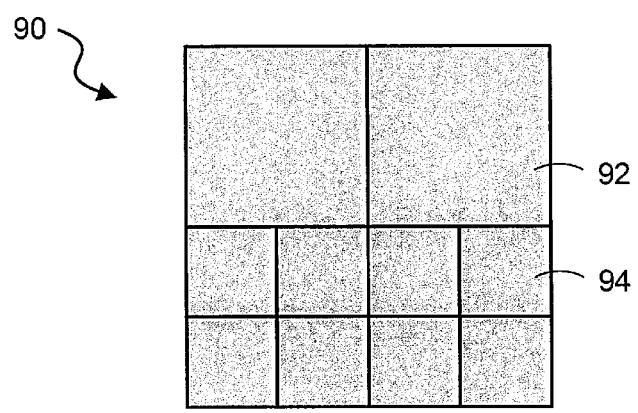
FIG. 5A is a schematic diagram of another hybrid pixel pattern design for use in a photon-counting detector in accordance with the present disclosure.

Referring now to FIG. 5A, a macro-pixel 90 having a different hybrid pixel pattern design from the design shown in FIG. 4B is shown. The macro-pixel 90 includes two large micro-pixels 92 and eight smaller micro-pixels 94. In this example the two large micro-pixels have a pixel size of 500 μm and the eight smaller micro-pixels have a pixel size of 250 μm within a macro-pixel 90 having an area of 1 mm×1 mm. The macro-pixel 90 includes 10 total micro-pixels in this design. This hybrid pixel pattern design still benefits from the use of two different sized micro-pixels within the macro-pixel 90 for both high flux and low flux scanning environments. Additionally, the use of two large micro-pixels and eight smaller micro-pixels may result in images with better resolution due to the addition of the larger micro-pixel.

Figure 5B:
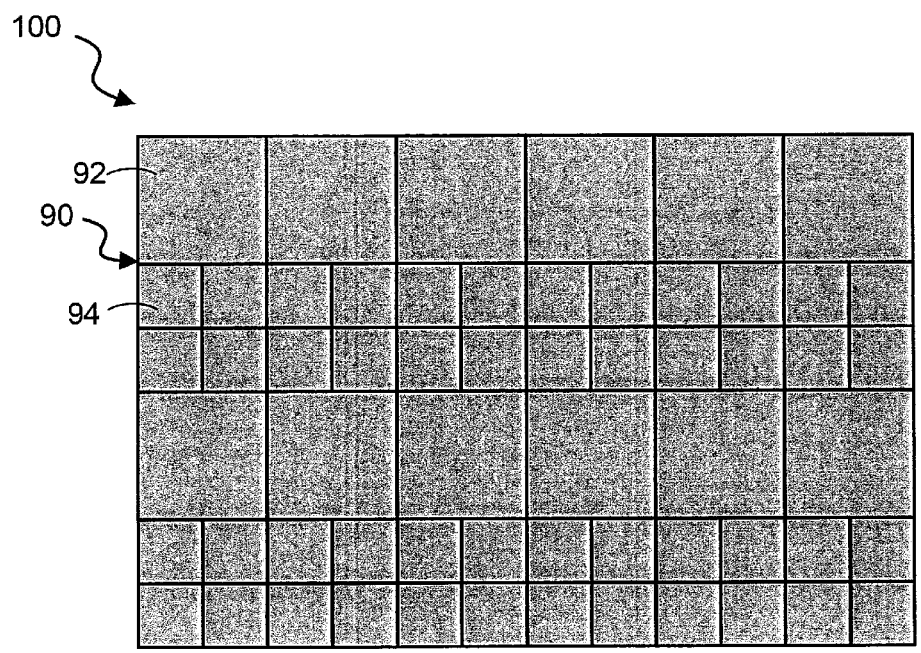
FIG. 5B is a schematic diagram of a group of six pixels incorporating the hybrid pixel pattern design of FIG. 5A in accordance with the present disclosure.

FIG. 5B illustrates a group of six macro-pixels 100 that includes the hybrid pixel pattern design of the macro-pixel 90 shown in FIG. 5A. The group of six macro-pixels is an example of what a portion of the photon-counting detector resembles on the anode surface.

Figure 5C:
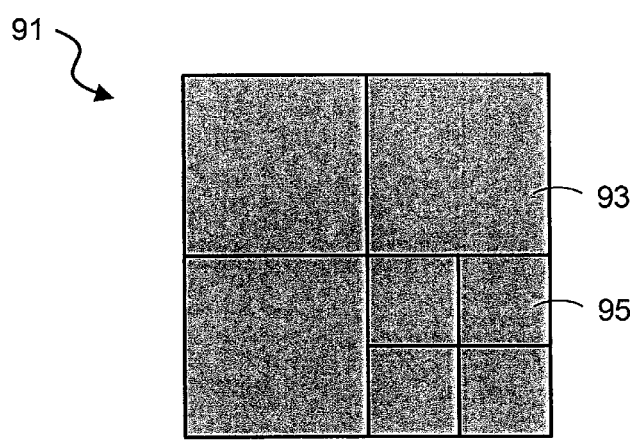
FIG. 5C is a schematic diagram of a hybrid pixel pattern design for use in a photon-counting detector in accordance with the present disclosure.

Referring now to FIG. 5C, a macro-pixel 91 having a different hybrid pixel pattern design from the design shown in FIGS. 5A and 5B is shown. The macro-pixel 91 includes three large micro-pixels 93 and four smaller micro-pixels 95. In this example the three large micro-pixels have a pixel size of 500 μm and the four smaller micro-pixels have a pixel size of 250 μm within the macro-pixel 91 having an area of 1 mm×1 mm. The macro-pixel 91 includes 7 total micro-pixels in this design. This hybrid pixel pattern design still benefits from the use of two different sized micro-pixels within the macro-pixel 91 for both high flux and low flux scanning environments. The use of three large micro-pixels and four smaller micro-pixels may result in images with better resolution.

High flux scanning environments may include a fast energy-resolved photon-counting x-ray imaging array using pixelated cadmium telluride (CdTe) semiconductor sensors and have achieved an output count rate (OCR) exceeding 100 million counts per second per square mm (Mcps/mm$^2$) measured with a clinical CT x-ray source. A fast application specific integrated circuit (ASIC) may be used with a two dimensional (2D) array of inputs for readout from pixelated CdTe or cadmium zinc telluride (CdZnTe) sensors. The 2D ASICs have four energy bins with a linear energy response across the entire dynamic range for clinical CT, which is between 30 keV and 140 keV. The uniform energy resolution over the entire dynamic range is an indication of good charge collection from the direct conversion sensors. The energy resolution is maintained at high flux over long varying exposure to x-rays indicating polarization free performance from the sensors. The results demonstrate fast output count rates from a clinical CT x-ray source, with good energy resolution and a low noise floor. The sensors and ASICs should be designed to fit into existing clinical CT systems.

Photon-counting detectors using CdTe or CZT substrates are promising candidates for CT systems but suffer from issues including charge sharing and pulse pileup. By using a hybrid pixel pattern design that incorporates an increased micro-pixel size for the detector to improve charge sharing characteristics without sacrificing at the expense of increasing pileup due to the use of smaller micro-pixels as well in order to minimize the increase of pulse pileup. The hybrid pixel pattern design is an important design consideration in CdTe detectors. Using the hybrid pixel pattern design allows for better results in both a high flux and low flux scanning environment without having to determine an optimal pixel size that is dependent on the specific task and on the charge shaping time.

In the hybrid pixel pattern design in this embodiment, detection data may be acquired by switching the micro-pixels to be used, for example, by using only small micro-pixels without using large micro-pixels if pileup occurs in the large micro-pixels.

For example, micro-pixels may be switched based on detection data at the time of scanogram imaging. Alternatively, micro-pixels may be switched by estimating a pileup state in the next view scanning, in which, if a value of detection data (such as an energy value) of one previous view is equal to or greater than a threshold value, the processing circuitry 44 (e.g., system control function 441 or pre-processing function 442) uses only the small micro-pixels in the next view scanning. This is not limited to one previous view. A size of micro-pixels used in the scanning target views may also be determined based on the value of detection data of views from two or more views prior. The present embodiment is not limited to this, and any general method of determining pileup of the detector data is applicable.

A size of the micro-pixels to be used may be determined in accordance with the position of the X-ray detector 12. For example, the small micro-pixels only are used at the end portion in the row direction and/or channel direction of the X-ray detector 12 where high flux X-ray irradiation is predicted, while both large micro-pixels and the small micro-pixels are used at the center portion in the row direction and/or channel direction of the X-ray detector 12 where low-flux X-ray irradiation is predicted. The end and center portions, for example, may be designated by the user, or determined automatically by the processing circuitry 44.

After the DAS 18 acquires detection data from the PCD 12, only detection data acquired with the small micro-pixels may be used without using detection data acquired with the large micro-pixels for subsequent processing (such as generation of a spectral image). Namely, switching may be performed in such a manner that detection data acquired with the small micro-pixels is kept, while detection data acquired with the large micro-pixels is abandoned.

As for determining whether to abandon detection data of large micro-pixels, the DAS 18 or the processing circuitry 44 (e.g., system control function 441 or pre-processing function 442) may determine that the detection data of large micro-pixels is not used (abandoned) if there is pileup in the energy detected at the large micro-pixels or if the energy of the detection data has a threshold value or more. Alternatively, when detection data is used, processing, such as reducing the weight of detection data of large micro-pixels and increasing the weight of detection data of small micro-pixels, may be performed.

By utilizing detection data of small micro-pixels where no pileup occurs, it is possible to improve reliability of the detection data and to increase detecting accuracy.

In contrast, in a low-flux scanning environment, only detection data of large micro-pixels may be used without using detection data of small micro-pixels.

In this case, similarly to the switching of the PCD 12 described above, micro-pixels used in the PCD 12 may be switched, or detection data may be acquired from the PCD 12 and only detection data of large micro-pixels may be used in the DAS 18 or the processing circuitry 44. Alternatively, the DAS 18 or the processing circuitry 44 may increase the weight of the detection data of large micro-pixels and reduce the weight of the detection data of small micro-pixels, and use the detection data for subsequent processing.

Since the PCD 12 of the present embodiment has two types of pixel patterns, calibration of the PCD 12 is easier when compared to the case in which the design of three or more pixel patterns is used.

The macro-pixels and the micro-pixels described above are conceptional. A configuration example of the X-ray detector 12 intended in reality will be described with reference to FIG. 6.

FIG. 6 illustrates an actual configuration example of the hybrid pixel pattern of FIG. 5C. As a macro-pixel 91 which is an example of the anode pixel 74, anode electrodes 99 (also referred to as "anode patterns") formed from materials with small electric resistance, such as metal, are formed on the crystal 71. They are electrically insulated or arranged with a non-continuous gap 97.

With the configuration of the anode electrode 99 and the gap 97, the hybrid pixel pattern of the large micro-pixels 93 and the small micro-pixels 95 is formed.

Figure 7A:
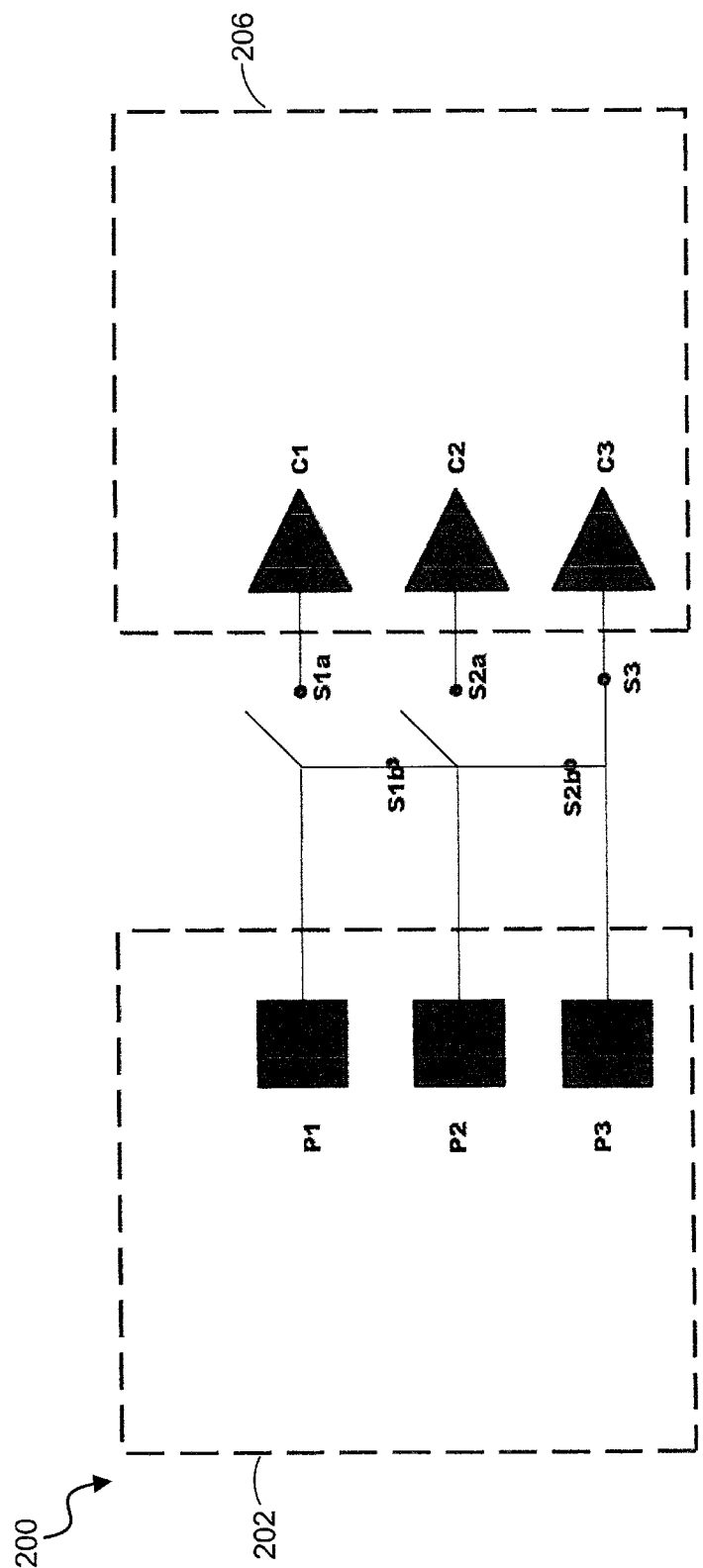
FIG. 7A illustrates a schematic diagram of the input channels from the pixels of the hybrid pixel pattern design and the corresponding amplifier and counter stages for reducing charge sharing in accordance with the present disclosure.

Referring now to FIG. 7A, the various micro-pixels of the hybrid pixel pattern design contain switches at the input stage 200 of an amplifier and counter. The channels that provide input to a given counter can be changed dynamically over the course of a CT scan or from scan to scan. This allows for configurable and dynamic management of the optimal effective pixel size and trade-off between pulse pileup in the amplifier/counter stage and cross talk in the detector pixel. Pixels P1, P2 and P3 can be of a uniform size and shape or, alternatively, of a mixed size and shape. For example, at low count rates (less than 10 Mcps/mm$^2$), pixel signals may be routed together into the same amplifier/counter stage thereby mitigating the detrimental effect of cross talk. Similarly, at high count rates such as 100 Mcps/mm$^2$ or greater, the pixel signals may be switched into separate amplifier/counter stage to mitigate the detrimental effect of pulse pileup.

The box 202 represents the input channels from the PCD having a hybrid pixel pattern design. P1, P2 and P3 in this example represent the micro-pixels which may include a combination of different sized micro-pixels. Each micro-pixel shown may be connected to an amplifier and counter stage shown in box 206 by a switch. In FIG. 7A, micro-pixel P1 may connect to amplifier and counter stage C1 via the switch S1$a$. Similarly, micro-pixel P2 can connect to C2 via the switch S2$a$ and micro-pixel P3 can connect to C3 via the switch S3. Alternatively, the switch S1$b$ may connect micro-pixels P1 and P2 and switch S2$b$ may connect micro-pixels P2 and P3. In FIG. 7A, the three micro-pixels shown (P1, P2, P3) are connected together by switches S1$b$ and S2$b$. In this illustrative example, signals from pixels P1 and P2 are routed to counter C3. This is achieved by having switches S1$a$ and S2$a$ open while switches S1$b$ and S2$b$ closed. When pixels P1, P2 and P3 are physically adjacent to each other, this creates an effective pixel size of P1+P2+P3 which may result in improved cross talk performance than pixels P1, P2, and P3 separately.

Figure 7B:
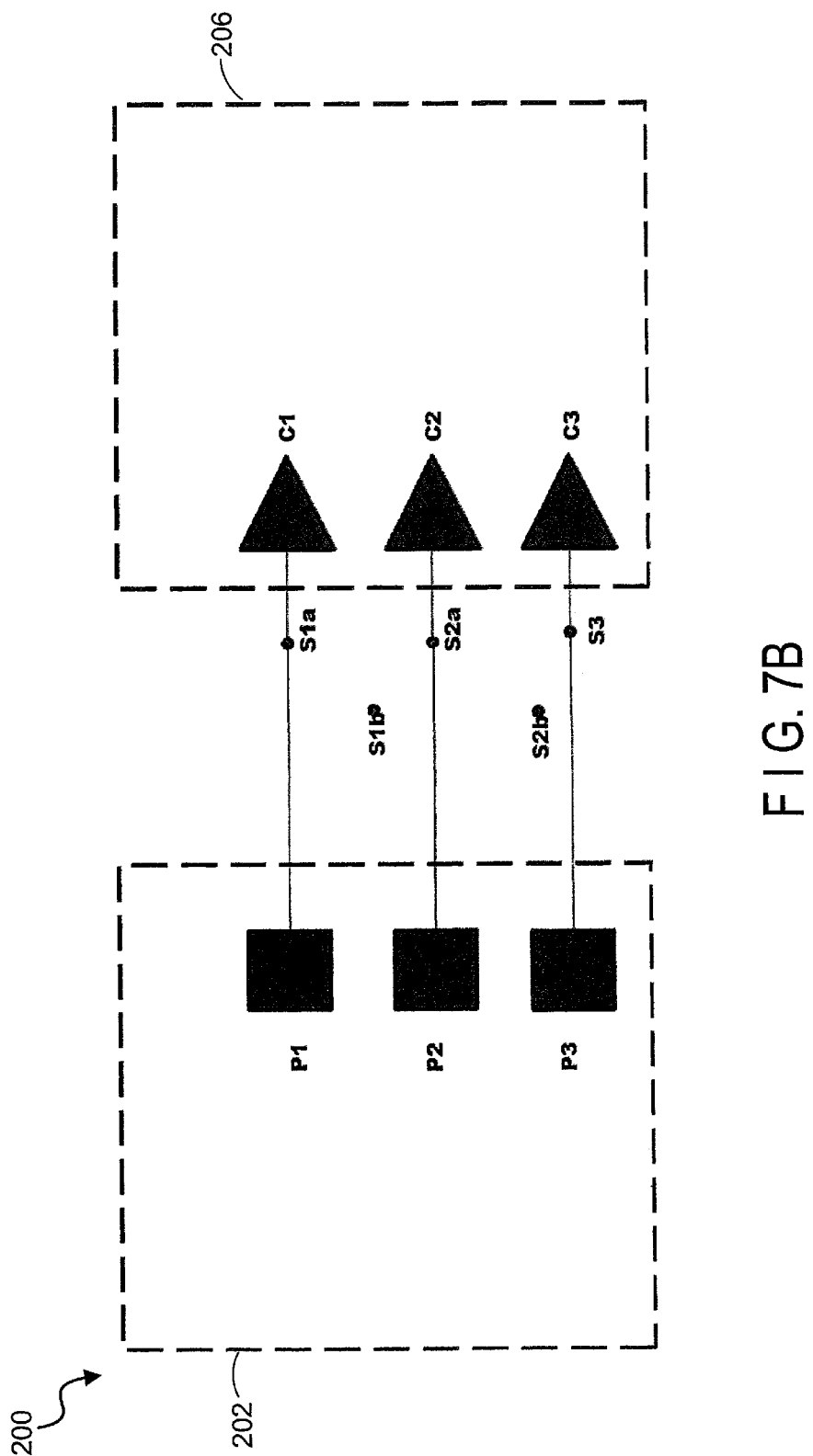
FIG. 7B illustrates a schematic diagram of the input channels from the pixels of the hybrid pixel pattern design and the corresponding amplifier and counter stages for minimizing pulse pile up issues in accordance with the present disclosure.
Figure 7C:
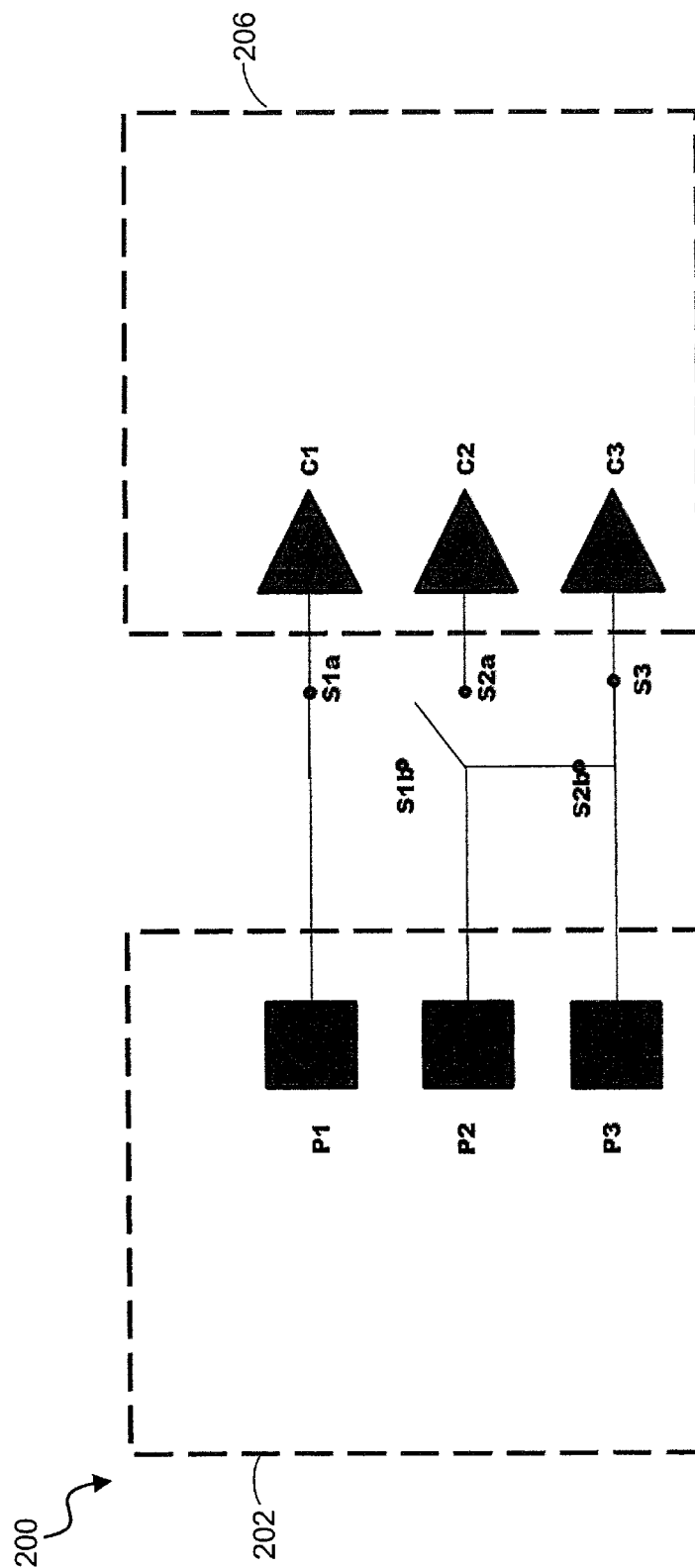
FIG. 7C illustrates a schematic diagram of the input channels from the pixels of the hybrid pixel pattern design and the corresponding amplifier and counter stages in accordance with the present disclosure.

FIG. 7B includes another illustrative example, the signal from pixel P1 is routed to counter C1 via switch S1$a$, the signal from pixel P2 is routed to counter C2 via S2$a$ and the signal from pixel P3 is routed to counter C3 via switch S3. Maintaining pixels separately may minimize pulse pileup issues and may be preferable in a high flux scanning environment. In FIG. 7C, the pixel P1 is routed to counter C1 via the switch S1$a$ and pixels P2 and P3 are routed to C3 via switches S2$b$ and S3. The channels that provide input to a particular counter may be changed dynamically in order to configure an optimal effective pixel size for the hybrid pixel pattern design associated with each macro-pixel of the photon-counting detectors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon-counting detector for acquiring projection data for generating a reconstructed image, comprising
a plurality of macro-pixels arranged on a semiconductor crystal having a first face and a second face, wherein the first face and the second face are parallel, wherein the plurality of macro-pixels each includes:
at least one large square micro-pixel disposed within the each macro-pixel, and
at least two small square micro-pixels disposed within the each macro-pixel, such that each of the at least two small square micro-pixels has a surface area that is less than a surface area of the at least one large square micro-pixel, wherein each side length of the at least one large square micro-pixel is greater than each side length of the at least two small square micro-pixels by an integer that is greater than 1.

2. The detector according to claim 1, wherein a half-length of one side of the macro-pixel corresponds to a length of at least one side of the large square micro-pixel, and a half-length of one side of the large square micro-pixel corresponds to a length of at least one side of the small square micro-pixel.

3. The detector according to claim 1, wherein the at least one large square micro-pixel has a pixel size within 300 to 600 μm.

4. The detector according to claim 1, wherein the at least two small square micro-pixels each have a pixel size within 150 to 300 μm.

5. The detector according to claim 1, wherein each macro-pixel includes one large square micro-pixel and twelve small square micro-pixels.

6. The detector according to claim 1, wherein each macro-pixel includes two large micro-pixels and eight small micro-pixels.

7. The detector according to claim 1, wherein each macro-pixel includes three large micro-pixels and four small micro-pixels.

8. The detector according to claim 1, wherein the plurality of macro pixels includes a 16×16 macro-pixel array comprising a total of 256 macro-pixels.

9. The detector according to claim 1, wherein the surface area of the at least one large square micro-pixel is twice as great as the surface area of each of the at least two small square micro-pixels.

10. The detector according to claim 1, further comprising: a first set of detector responses corresponding to the at least one large square micro-pixel; and a second set of detector responses corresponding to the at least two small square micro-pixels.

11. The detector according to claim 10, wherein information obtained from the first set of detector responses corresponding to the at least one large square micro-pixel is used to calibrate the at least two small square micro-pixels in a low-flux scanning environment.

12. The detector according to claim 10, wherein information obtained from the second set of detector responses corresponding to the at least two small square micro-pixels is used to calibrate the at least one large square micro-pixel in a high-flux scanning environment.

13. The detector according to claim 1, further comprising a cathode electrode covering the first face, the plurality of macro-pixels covering the second face.

14. An X-ray CT apparatus, comprising: an X-ray tube configured to emit X-rays; and the detector according to claim 1, configured to detect X-rays that have been emitted from the X-ray tube and have passed through a subject.

15. The detector according to claim 1, wherein the plurality of macro-pixels each includes:
   a large square micro-pixel disposed at a respective center of the respective macro-pixel, and
   the at least two small square micro-pixels disposed adjacent each edge of the respective large square micro-pixel.

16. A photon-counting detector, comprising
   a plurality of macro-pixels arranged on a semiconductor crystal having a first face and a second face, wherein the first face and the second face are parallel, wherein the plurality of macro-pixels each includes:
      a large micro-pixel disposed at a respective center of the respective macro-pixel, and
      N small micro-pixels disposed adjacent each edge of the respective large micro-pixel,
   wherein each of the N small micro-pixels disposed adjacent each edge of the respective large micro-pixel has a surface area that is less than a surface area of the large micro-pixel.

17. The detector according to claim 16, wherein N is 4 such that the each respective large micro-pixel is disposed in the respective center portion of each of the plurality of macro-pixels with the twelve small micro-pixels forming a respective periphery around the each respective large micro-pixel.

18. A photon-counting detector for acquiring projection data for generating a reconstructed image, comprising
   a plurality of macro-pixels arranged on a semiconductor crystal having a first face and a second face, wherein the first face and the second face are parallel, wherein the plurality of macro-pixels each includes:
      a large micro-pixel disposed within the each macro-pixel and at least two small micro-pixels disposed within the each macro-pixel, wherein a half-length of one side of the macro-pixel corresponds to a length of at least one side of the large micro-pixel, and
      each of the at least two small micro-pixels having a surface area that is less than a surface area of the large micro-pixel.

19. A photon-counting detector for acquiring projection data for generating a reconstructed image, comprising
   a plurality of macro-pixels arranged on a semiconductor crystal having a first face and a second face, wherein the first face and the second face are parallel, and wherein the plurality of macro-pixels each includes:
      a large micro-pixel disposed within the each macro-pixel and at least two small micro-pixels disposed within the each macro-pixel, wherein information obtained from detector responses corresponding to the at least one large micro-pixel is used to calibrate the at least two small micro-pixels in a low-flux scanning environment, and
      each of the at least two small micro-pixels having a surface area that is less than a surface area of the large micro-pixel.

* * * * *